(12) United States Patent
Fontana

(10) Patent No.: US 12,415,063 B2
(45) Date of Patent: Sep. 16, 2025

(54) CONNECTORS FOR PERITONEAL DIALYSIS

(71) Applicant: Bellco S.R.L., Mirandola (IT)

(72) Inventor: Marco Fontana, Mirandola (IT)

(73) Assignee: Bellco S.R.L., Mirandola (IT)

( * ) Notice: Subject to any disclaimer, the term of this patent is extended or adjusted under 35 U.S.C. 154(b) by 258 days.

(21) Appl. No.: 17/520,425

(22) Filed: Nov. 5, 2021

(65) Prior Publication Data

US 2022/0184369 A1 Jun. 16, 2022

(30) Foreign Application Priority Data

Dec. 10, 2020 (EP) ..................................... 20213145

(51) Int. Cl.
*A61M 39/10* (2006.01)
*A61M 1/28* (2006.01)

(52) U.S. Cl.
CPC ............ *A61M 39/10* (2013.01); *A61M 1/285* (2013.01); *A61M 2039/1027* (2013.01); *A61M 2039/1077* (2013.01)

(58) Field of Classification Search
CPC .. A61M 2039/1033; A61M 2039/1027; A61M 39/12; A61M 2039/1038; A61M 39/10; A61M 39/20; F16K 7/061; F16K 7/065; F16K 7/066; F16L 19/0225; F16L 2201/44; F16L 37/38
See application file for complete search history.

(56) References Cited

U.S. PATENT DOCUMENTS 5,176,415 A * 1/1993 Choksi .................. A61M 39/10
285/332.1
11,602,607 B2 * 3/2023 Lau .................... A61M 16/0672
(Continued)

FOREIGN PATENT DOCUMENTS

EP 0499718 A1 8/1992
EP 953365 A2 * 11/1999 ............ A61M 39/12
(Continued)

OTHER PUBLICATIONS

Extended Search Report from counterpart European Application No. 20213145.4 dated May 31, 2021, 7 pp.
(Continued)

*Primary Examiner* — Courtney B Fredrickson
*Assistant Examiner* — Kayla M. Turkowski

(57) ABSTRACT

In some examples, a connector assembly configured to connect a tube to a peritoneal dialysis cycler comprises: a connector piece having a bore, wherein a proximal end of the bore defines an opening in a proximal portion of the connector piece configured to receive and deliver fluid from and to the cycler; and a connector body having a bore, wherein a proximal end of the bore defines a cavity in a proximal portion of the connector body configured to receive a distal portion of the connector piece to position the distal end of the bore of the connector piece in fluid communication with the proximal end of the bore of the connector body. The distal portion of the connector body comprises a tubular portion configured to form an interference fit with the tube. A collar of the connector body is configured to grip an outer surface of the tube.

17 Claims, 3 Drawing Sheets

(56) References Cited

U.S. PATENT DOCUMENTS

| | | | |
|---|---|---|---|
| 2008/0228125 A1* | 9/2008 | Brugger | A61M 39/0208 604/6.16 |
| 2014/0316332 A1* | 10/2014 | Lo | A61M 1/1666 604/28 |
| 2017/0000998 A1* | 1/2017 | Guala | A61M 39/10 |
| 2022/0008708 A1* | 1/2022 | Takeuchi | A61M 39/10 |
| 2023/0001176 A1* | 1/2023 | Otto | B29C 65/4895 |
| 2023/0210727 A1* | 7/2023 | Coussegal | A61J 15/0061 604/533 |

FOREIGN PATENT DOCUMENTS

| | | | |
|---|---|---|---|
| FR | 2703593 A1 | 10/1994 | |
| WO | 2015114428 A1 | 8/2015 | |
| WO | 2017176701 A1 | 10/2017 | |

OTHER PUBLICATIONS

Response to Extended Search Report dated May 31, 2021, from counterpart European Application No. 20213145.4 filed Dec. 14, 2022, 15 pp.

* cited by examiner

CONNECTORS FOR PERITONEAL DIALYSIS

This application claims priority from European Patent Application No. 20213145.4, filed Dec. 10, 2020, and entitled, "CONNECTORS FOR PERITONEAL DIALYSIS," the entire content of which is incorporated herein by reference.

FIELD OF THE INVENTION

The present invention relates to connectors for connecting a patient catheter, in particular a patient catheter transfer set, to a peritoneal dialysis cycler.

BACKGROUND OF THE INVENTION

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function are conventionally treated with dialysis. Dialysis removes waste, toxins and excess water from the body that would otherwise have been removed by normal functioning kidneys. Dialysis treatment for replacement of kidney functions is life-saving for many patients.

Hemodialysis and peritoneal dialysis are two types of dialysis therapies commonly used to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood back to the patient. A large amount of dialysate, for example about 120 liters, is used to dialyze the blood, during a single hemodialysis therapy. The spent dialysate is then discarded. Hemodialysis treatment lasts several hours and is generally performed in a treatment center about three or four times per week.

Peritoneal dialysis utilizes a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, since the dialysate is formulated to have a higher osmolality than blood. The spent dialysate is drained from the patient's peritoneal cavity after a suitable interval, which removes the waste, toxins and excess water in the spent dialysate from the patient. This cycle is repeated, typically 3-4 times.

There are various types of peritoneal dialysis therapies, including continuous ambulatory peritoneal dialysis ("CAPD"), automated peritoneal dialysis ("APD") and continuous flow peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and infuses fresh dialysate through the catheter and into the patient's peritoneal cavity. The fresh dialysate is normally heated to body temperature before infusion, for example on a heating plate. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines fluidly connect to an implanted catheter. The APD machines also fluidly connect to a source or bag of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles will occur during APD. A "last fill" is typically used at the end of APD, which remains in the peritoneal cavity of the patient when the patient disconnects from the dialysis machine for the day. API) frees the patient from having to manually performing the drain, dwell, and fill steps.

A typical system for CAPD is described in EP-A-0499718. It comprises a stand which is about 2 meters high. At a first upper level, at the upper end of the stand, there are hooks for hanging bags containing ready-mixed supply solution for peritoneal dialysis. The supply bags are connected via tubes to a heat bag positioned just below the supply bags at a second intermediate level. The heat bag is positioned on a heating surface of a weighing device.

The heat bag is filled, under control of valves, from the supply bags and may have a volume of about 2 litres or slightly more. When the contents in the heat bag has achieved the correct temperature, this is fed by gravity to a catheter terminating in the abdominal cavity of the patient. The catheter and the abdominal cavity are at a third level which is below the second level.

When the dialysis solution has fulfilled its task it is drained to a discharge bag positioned on a fourth level. The discharge bag is attached to a hook arrangement which hangs on the weighing device for the heat bag. In this way the same weight measuring element or load cell is used for weighing the heat bag as well as the discharge bag. The contents of the discharge bag are finally drained either directly to a drain or to collection bags which are situated on a fifth and lowest level.

In order to minimize trauma to the implanted peritoneal dialysis catheter caused by frequent clamping during peritoneal dialysate exchange procedures, the catheter is typically connected to a so-called transfer set by means of a twist clamp such as a leer lock. The transfer set is a short extension of the peritoneal catheter that can be replaced every few months, or more often if contamination is suspected. The transfer set is a length of catheter-like tubing having, typically a leer lock or similar attachment at one end for attaching the transfer set to the implanted catheter, and a similar attachment at the other end for attaching the transfer set to the peritoneal dialysate cycler.

Due to the importance of the catheters and transfer set in carrying out dialysis procedures, it is vitally important that the connections involved in such processes are secure, leak-proof, properly aligned, and easily connectable. This is particularly important in the case of connection of tubes which need to be manually connected following implantation into a patient. Since many of these devices are intended for use by a patient on an outpatient basis, such as in the home, without the supervision of a healthcare professional, it is important that the connections remain secure and in proper position so that there is no leakage or improper delivery of dialysis fluid. It is thus important that such connections be made as simply and effectively as possible so that secure and mistake-proof connections can readily be made manually following implantation of the catheter into a patient. In addition, the it should be possible to make the connections in such a way as to minimized microbial contamination of any surfaces that will come into contact with the dialysate in order to minimise the risk of peritonitis. Since the connectors are located adjacent to the body of the patient, they should be made as small and as light as possible. Finally, it would be desirable to provide an emergency cut-off mechanism in the connector, whereby liquid flow through the connector can be stopped by the user at any time without loss of sterility.

SUMMARY OF THE INVENTION

The present invention relates generally to connectors for connecting an external end of an implanted catheter or catheter transfer set to a source of peritoneal dialysate and/or to a drain for effluent peritoneal dialysate and/or to a peritoneal dialysate cycler.

In a first aspect, the present invention provides a connector assembly for connecting a catheter tube, or the tube of a catheter transfer set, to a peritoneal dialysis cycler, the connector comprising: a connector piece having a proximal portion and a distal portion and having a bore extending longitudinally therethrough, wherein a proximal end of the bore defines an opening in a proximal portion of the connector piece for receiving and delivering fluid from and to a peritoneal dialysis cycler, and a distal end of the bore defines an opening in the distal portion of the connector; a connector body having a proximal portion and a distal portion and having a bore extending longitudinally therethrough, wherein a proximal end of the bore defines a cavity in the proximal portion of the connector body configured to receive the distal portion of the connector piece to position the distal end of the bore of the connector piece in fluid communication with the proximal end of the bore of the connector body, the distal portion of the connector body comprising a tubular portion configured to form an interference fit with an end of the tube, and wherein the connector body further comprises a distally extending collar configured to grip an outer surface of the tube when the tube forms the said interference fit with the tubular portion.

In a further aspect, the present invention provides a connector assembly according to the present invention having a peritoneal dialysis catheter attached to the distal end of the connector body in fluid communication with the bore of the connector body.

In a further aspect, the present invention provides a connector assembly according to the present invention having a tube of a peritoneal dialysis transfer set attached to the distal end of the connector body in fluid communication with the bore of the connector body.

In a further aspect, the present invention provides a connector assembly according to any of the above aspects of the invention having a source of peritoneal dialysate attached to the proximal end of the connector piece, in fluid communication with the bore of the connector piece.

The connector assemblies of the present invention may be provided as the assembled connector, or as a kit of parts comprising the connector piece and the connector body. In embodiments, the kit of parts may further comprise a clamping collar. In embodiments, the kit of parts may further comprise a cap or other obturating device configured to be secured to the proximal end of the connector body in liquid-tight fashion to seal off the catheter or transfer set when it is not in use for introduction or removal of dialysate to or from the patient. In embodiments, the kit of parts may comprise a cap configured to be secured to the distal end of the connector piece in liquid-tight fashion to seal off the dialysis cycler line when it is not in use for introduction or removal of dialysate to or from the patient. Alternatively or additionally, the kit of parts may comprise a peritoneal dialysis transfer set.

Further features which may suitably be present in the connector assemblies according to any aspect of the invention are disclosed in the accompanying dependent claims.

DETAILED DESCRIPTION OF THE INVENTION

Figure 1:
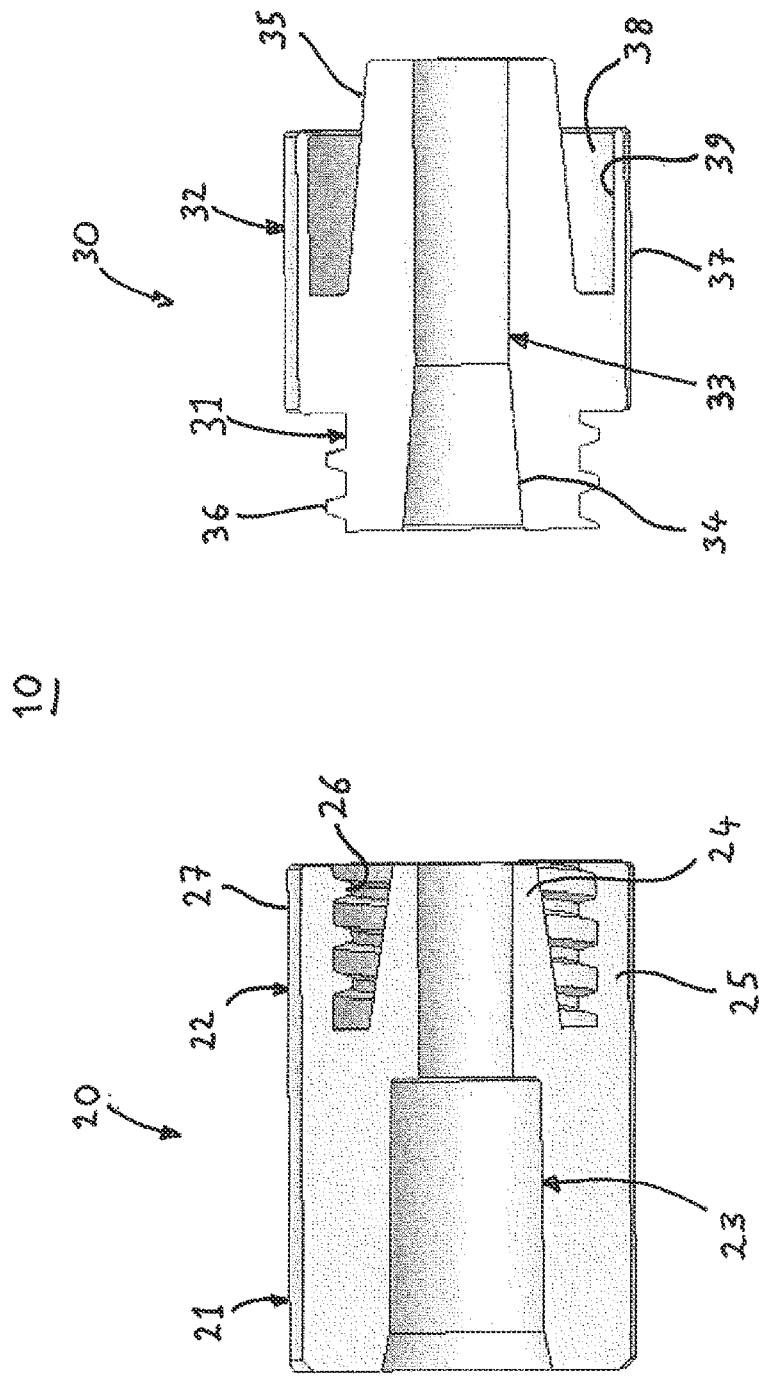
FIG. 1 shows a longitudinal cross-sectional view of a first embodiment of a connector assembly according to the invention.

In a first aspect, the present invention provides a connector assembly for connecting a catheter tube, or a catheter transfer set tube to a peritoneal dialysis cycler, the connector comprising: a connector piece having a proximal portion and a distal portion and having a bore extending longitudinally therethrough, wherein a proximal end of the bore defines an opening in a proximal portion of the connector piece for receiving and delivering fluid from and to a peritoneal dialysis cycler, and a distal end of the bore defines an opening in the distal portion of the connector; a connector body having a proximal portion and a distal portion and having a bore extending longitudinally therethrough, wherein a proximal end of the bore defines a cavity in the proximal portion of the connector body configured to receive the distal portion of the connector piece to position the distal end of the bore of the connector piece in fluid communication with the proximal end of the bore of the connector body, the distal portion of the connector body comprising a tubular portion configured to form an interference fit with an end of the tube, and wherein the connector body further comprises a distally extending collar configured to grip an outer surface of the tube when the catheter forms said interference fit with the tube.

Suitably, at least a portion of the distal portion of the connector piece has a distally tapered outer surface for forming an interference fit with a correspondingly tapered inner surface of the proximal end of the bore of the connector body.

Suitably, the connector piece and the connector body comprise complementary releasable securing elements for releasably securing the connector piece to the connector body.

In these embodiments, the distal portion of the connector piece may comprise a central nozzle and a cylindrical skirt portion extending distally around and radially spaced from the central nozzle, the cylindrical skirt portion defining a first thread on an internal surface thereof, and the proximal portion of the connector body is correspondingly provided with a second thread on an outer surface thereof for releasably securing the connector body to the connector piece by engagement of the first thread and the second thread.

Alternatively or additionally, the complementary releasable securing elements may comprise snap-fitting elements, for example the snap-fitting elements may comprise one or more flexible arms fixed to the connector piece, wherein the flexible arms engage complementary recesses in the connector body for releasably securing the connector piece to the connector body.

Suitably, the distal portion of the connector body may comprise a tapered nozzle for forming an interference fit with an interior surface of the end of the tube. In these embodiments, an inner surface of the collar and an outer surface of the distal tubular portion may define an annular gap therebetween for receiving a tubular wall of the tube, and wherein the width of the annular gap tapers proximally.

Alternatively, the distal portion of the longitudinal bore of the connector body may be configured to receive the tube and to form an interference fit with an outer surface thereof. In these embodiments, the distal portion of the longitudinal bore of the connector body may comprise one or more inwardly extending annular sealing elements and/or one or more barbs for retaining the tube.

In embodiments, the distally extending collar of the connector body may comprise one or more inwardly extending radial projections for gripping the outer surface of the tube.

In embodiments, a distal end of the collar is located distally of the distal end of the longitudinal bore of the connector body.

In any embodiment, the connector assembly may comprise a cut-off mechanism that can be actuated to block liquid flow through the connector. For example, the distally extending collar of the connector body may comprise a segmented collar having a plurality of circumferentially spaced distally extending segments separated by an equal plurality of gaps, each segment having a distal flange proximal to a distal end thereof and extending radially inwardly, the connector assembly further comprising a clamping collar having a bore with a distally tapered internal surface, such that proximal movement of the clamping collar onto the distal portion of the connector body causes the internal surface of the clamping collar bore to abut the distally extending segments to drive the distally extending segments radially inwardly to cut off a liquid path through the connector by engagement of the distal flanges with the tube.

In these embodiments, complementary threads may be provided on the outer surface of the distal portion of the connector body and on an inner surface of a proximal portion of the clamping collar, whereby screwing the clamping collar onto the distal portion of the connector body drives the clamping collar proximally onto the connector body to cut off the liquid path through the connector.

In any embodiment, the distal portion of the connector body and the distally extending collar may be integrally formed in one piece. Suitably, all components of the connector body may be integrally formed in one piece.

The connector assembly of the present invention may further comprise a peritoneal dialysis catheter transfer set attached to the distal end of the connector body in fluid communication with the bore of the connector body.

Alternatively or additionally, the connector assembly of the present invention may further comprise a source of peritoneal dialysate attached to the proximal end of the connector piece in fluid communication with the bore of the connector piece.

The connector assemblies according to the present invention (including the kit-of-parts) are suitably sterile, and may be packaged in a microorganism-impermeable container. One or more surfaces of the connector assemblies according to the present invention may comprise an antimicrobial material, such as silver, an antibiotic, triclosan or chlorhexidine.

The connector assemblies according to the present invention suitably weigh from about 1 g to about 100 g, for example from about 10 g to about 50 g. The maximum longitudinal dimension of the connector assemblies according to the first aspect when assembled is suitably from about 1 cm to about 10 cm, for example from about 1 cm to about 4 cm. The maximum transverse dimension of the connector assemblies according to the first aspect when assembled is suitably from about 5 mm to about 15 mm, for example from about 8 mm to about 12 mm.

The term "catheter" herein refers to a catheter suitable for administration of peritoneal dialysate to a human patient. Such catheters are suitably formed from a medically acceptable elastomer such as silicone. The catheter is suitably substantially cylindrical and tubular, with an internal diameter of about 2 mm to about 5 mm, for example about 3 mm to about 4 mm, a wall thickness of from about 0.4 mm to about 1.5 mm, for example about 0.6 mm to about 1 mm, and an outside diameter of from about 3 mm to about 8 mm, for example about 4 mm to about 6 mm. The catheter may comprise a transfer set attached to the end thereof. In these embodiments, the tubular portion at the distal portion of the connector body is configured to form an interference fit with an end of the transfer set tube. The transfer set tube is suitably as described above in relation to the catheter tube.

The term "peritoneal dialysis cycler" herein refers to any apparatus for supplying peritoneal dialysate for administration to a human patient, and/or for receiving effluent peritoneal dialysate from a human patient for disposal or recycling. The peritoneal dialysis cycler suitably comprises a source of peritoneal dialysate for administration to a human patient and a fluid channel for supplying the peritoneal dialysate from the source to the proximal end of the connector assemblies of the present invention. The fluid channel may comprise or consist of a combined administration and effluent channel, in which the peritoneal dialysis cycler supplies fresh peritoneal dialysate and receives effluent dialysate through the same channel at different stages of the dialysis procedure. The peritoneal dialysis cycler may comprise one or more further components that are known in the relevant art, such as valves for switching between supply of fresh dialysate and receipt of effluent dialysate through the channel, a waste bag for receiving effluent dialysate, a heater for heating fresh dialysate prior to administration, a weighing device for determining the weight of dialysate supplied or received from the patient at different points in the procedure, automatic control devices for automated peritoneal dialysis (APD), and dialysis membranes for recycling. A suitable peritoneal dialysis cycler is described, for example, in WO2017/176701.

The term "peritoneal dialysate" herein refers to an aqueous solution suitable for administration to a human patient for performing peritoneal dialysis. Peritoneal dialysate suitably contains sodium, calcium and magnesium salts such as chlorides and lactates, and an osmolality increasing agent such as glucose of icodextrin. Peritoneal dialysate is suitably hypertonic (346-485 mmol/l) and buffered to pH 5-6. Peritoneal dialysate is suitably sterile.

The term "liquid-tight connection" herein refers to a leak-free fluid connection, whereby liquid can flow along the desired pathway between longitudinal bores of the components without leaking from the assembly or the couplings of the assembly at pressures conventionally used for moving liquids in peritoneal dialysis equipment. A coupling is considered to be leak free if there is no visible liquid leakage when the coupling contains water at a gauge pressure of 0.05 bar (5 kN).

The terms "proximal" and "distal" herein are relative terms the meaning of which will be apparent from the following description of specific embodiments. Briefly, "proximal" components are upstream of "distal components" when liquid is flowing through the connector from the peritoneal dialysis cycler towards the catheter or transfer set.

FIG. 1. shows a longitudinal cross-section through a first embodiment of a connector assembly 10 according to the invention. The connector assembly comprises a connector piece 20 and a connector body 30. The connector piece 20 is integrally formed in one piece from a medically acceptable thermoplastic, for example by injection molding. The connector piece comprises a proximal portion 21 and a distal portion 22. A longitudinal bore 23 extends longitudinally and substantially centrally through the connector piece.

The proximal portion 21 of the connector piece is configured for substantially liquid-tight connection to an inlet and/or effluent line of the peritoneal dialysis cycler such that the longitudinal bore is in liquid communication with the said inlet and/or effluent line.

The distal portion 22 of the connector piece comprises a central, tapered nozzle 24 having the longitudinal bore 23 extending therethrough and a cylindrical skirt 25 which is concentric with the nozzle 24 and the bore 23 and radially spaced from the nozzle 24. A thread 26 is integrally formed on the radially interior surface of the cylindrical skirt 25. The outer surface 27 of the cylindrical skirt 25 is substantially cylindrical and contiguous with the outer surface of the remainder of the connector piece, whereby the connector piece has overall a substantially cylindrical outer surface. Longitudinal ribs may be provided on the outer surface 27 of the cylindrical skirt.

The connector body 30 has a proximal portion 31 and a distal portion 32 and a central longitudinal bore 33. The connector body 30 is integrally formed in one piece from a medically acceptable thermoplastic, for example by injection molding. The proximal portion 34 of the central longitudinal bore 33 is tapered radially outwardly so that it forms (in the assembled connector assembly) an interference fit with the tapered nozzle 24 of the connector piece 20 with the longitudinal bores 23, 33 of the connector piece 20 and the connector body in liquid-tight fluid communication. The large area of the interference fit helps to ensure liquid-tight engagement of the connector piece and the connector body without the need for excessive tightening or securing forces being applied by the user. Sealing may further be enhanced by provision of one or more circumferential sealing features, such as a circumferential rib or O-ring, on the tapered nozzle 24 or the interior surface of the proximal portion 34 of the longitudinal bore 33.

An outer surface of the proximal portion 31 of the connector piece is provided with an integral thread 36 that is complementary with the internal thread 26 of the cylindrical skirt 25 for securing the connector body to the connector piece. Suitably, the threads are configured to be easy to secure and release, for example by inexperienced or physically weak users. Thus, for example, the threads 36, 26 may be fast-turn threads, having a high thread pitch, so that the connector body can be released from a fully secured to a fully released position on the connector piece by relative rotation through 360 degrees or less. Alternatively or additionally, the threads 36, 26 may be multi-start threads, such as two-start or four-start threads, whereby less relative rotation of the connector body and the connector piece may be needed to engage the threads. Alternatively, the threads may be replaced by other suitable quick-attachment devices, such as complementary bayonet fittings or snap fittings on the proximal portion 31 of the connector piece or the internal thread 26 of the cylindrical skirt 25.

The distal portion 32 of the connector body 30 comprises a central nozzle 35 through which the central bore 33 extends. The outer surface of the central nozzle 35 is in the form of a tapered truncated cone and is configured to form an interference fit within the bore of a patient catheter transfer set tube (not shown) to provide liquid-tight connection between the connector body 30 and the tube of a catheter transfer set, with the bore 33 of the connector body in communication with the bore of the tube to provide liquid communication through the connector for dialysate. The outer surface of the central nozzle 35 may comprise one or more circumferential ribs to improve gripping and sealing against the interior surface of the tube. The circumferential ribs may be configured to provide increased resistance to removal of the catheter transfer set tube from the nozzle than to insertion of the nozzle into the tube. For example, the circumferential ribs may have a saw-tooth shape in longitudinal cross-section, with a greater slope on the proximal side of the saw tooth than on the distal side of the saw tooth.

The distal portion 32 of the connector body 30 further comprises a distally extending collar 37 extending around and radially spaced from the central nozzle so as to leave an annular socket 38 between the central nozzle 35 and the inner surface 39 of the distally extending collar 37. This socket 38 is configured to receive the tubular wall of an end of a catheter transfer set tube when the tube is pushed onto the central nozzle 35 with the central nozzle 35 forming an interference fit with the bore of the tube. The longitudinal taper of the nozzle 35 is greater than the longitudinal taper of the inner surface 39 of the distally extending collar 37, whereby the radial width of the socket 38 decreases from the open, distal end of the socket towards the closed, proximal end of the annular socket. The effect of this is that the outer surface of the tube is progressively engaged and gripped by the inner surface 39 to engage and grip the outer wall of the tube and thereby securely attach the tube to the connector body by simply pushing the tube into the distal end of the connector body. Suitably, the inner surface 39 may be cylindrical, i.e. it may have no taper. The taper of the annular socket is then provided entirely by the taper of the central nozzle outer wall. The inner surface 39 may comprise one or more surface gripping elements, such as circumferential ribs. The gripping elements may be configured to provide increased resistance to removal of the tube from the socket than to insertion of the tube from the socket. For example, the gripping elements may comprise circumferential ribs having a saw-tooth shape in longitudinal cross-section, with a greater slope on the proximal side of the saw tooth than on the distal side of the saw tooth.

Figure 2:
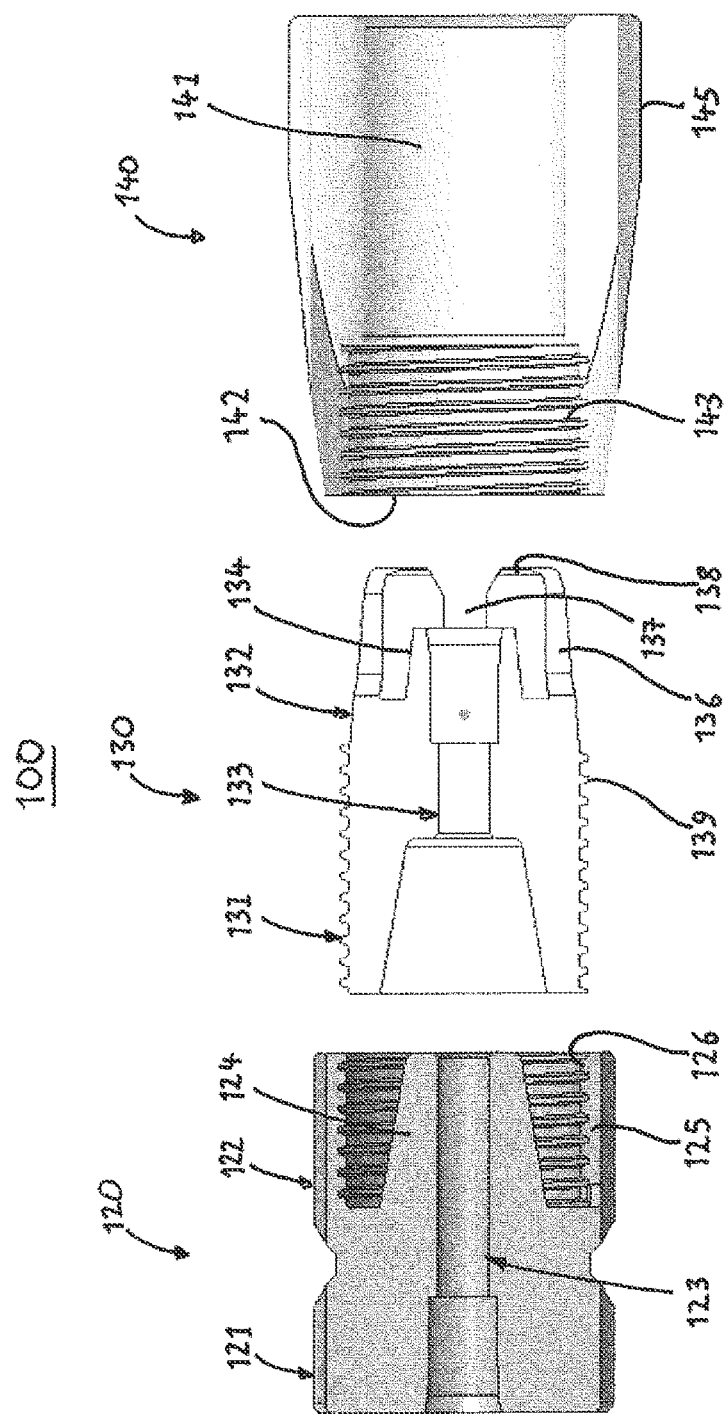
FIG. 2 shows a longitudinal cross-sectional view of a second embodiment of a connector assembly according to the invention.

Referring to FIG. 2, the connector assembly 100 according to this embodiment comprises a connector piece 120, a connector body 130, and a clamping collar 140. The connector piece 120 comprises a proximal portion 121, a distal portion 122, and a central longitudinal bore 123. The distal portion of the connector piece 120 comprises a central tapered nozzle 124, and a cylindrical skirt 125 having an internal thread 126 extending distally around and radially spaced from the nozzle. The connector body 130 comprises a proximal end 131, a distal end 132, and a central longitudinal bore 133. The connector piece 120 and the proximal end 131 of the connector body are substantially similar in structure and operation to the corresponding elements of the embodiment of FIG. 1, and therefore will not be described further.

The distal end 132 of the connector body 130 comprises a central, distally-extending tapered nozzle 134 for forming an interference fit with an internal surface of an end of a catheter. The central nozzle 134 is similar to, and performs the same function, as the central nozzle 35 of the embodiment of FIG. 1, and therefore will not be described further. The distal end 132 of the connector body 130 further comprises a distally extending split collar comprising four identical arcuate (in transverse section) elements 136 circumferentially spaced around and radially spaced from the central nozzle 134. There may be more or fewer arcuate elements in alternative embodiments, for example there may be 2, 3, 4, 5, 6, or more arcuate elements 136. Circumferential gaps 137 are defined between the arcuate elements 136. Each arcuate element 136 has a tip flange 138 extending radially inwardly. The arcuate elements 136 extend distally beyond the distal-most end of the central nozzle 134. An external thread 139 is provided on an outer surface of the connector body proximal to the arcuate elements 136. All elements of the connector body 130 are suitably formed integrally in one piece, for example by injection molding of a medically acceptable thermoplastic.

The clamping collar 140 is likewise suitably formed integrally in one piece, for example by injection molding of a medically acceptable thermoplastic. It comprises a longitudinal central bore 141 having an open proximal portion 142 having an internal thread 143 that is complementary to the external thread 139 on the distal portion of the connector body to enable the clamping collar to be screwed onto the distal end of the connector body. The complementary threads 139, 143 may be configured as described above for the complementary threads 26, 35 on the connector piece and the proximal portion of the connector body. The central bore 141 of the clamping collar 140 further comprises a tapered portion 143 located distally of the proximal portion 141, wherein the tapered portion tapers distally (as shown in the clamping collar of FIG. 3). In use, the clamping collar is initially fitted over a transfer set tube by sliding the tube through the central longitudinal bore of the clamping collar 140. The end of the tube is then inserted onto the distal end of the connector body 130 such that an interior surface of the tube lumen forms an interference fit with the tapered outer surface of the central nozzle 135 as disclosed above in relation to the embodiment of FIG. 1.

The clamping collar 140 and arcuate elements 136 provide a cut-off feature to block flow of liquid through the connector assembly. The cut-off is actuated by screwing the clamping collar 140 down onto the distal end 132 of the connector body 130 by means of the complementary threads 139, 143. This causes radially outer surfaces of the arcuate elements 137 to abut an interior surface of the tapered portion of the central bore 141. Further screwing down of the clamping collar 140 thereby cams the arcuate elements 136 radially inwardly until the tip flanges 138 engage and clamp the outer surface of the tube to block the liquid flow path. The outer surface of the clamping tube is provided with a plurality of radially projecting, longitudinally extending flanges 145 to provide improved grip when rotating the clamping collar.

It will be appreciated that the complementary threads 139, 143 of the above cut-off feature may be replaced by alternative engagement means to advance the clamping collar 140 proximally along the connector piece 130 by rotating the clamping collar 140. For example, one or more pins may be provided on the clamping collar or on the outer surface of the connector piece to engage one or more complementary helical slots on the connector piece or the clamping collar. The slots may comprise a bayonet-type portion having zero or negative pitch at the inner end thereof to lock the clamping collar in the cut-off position.

Figure 3:
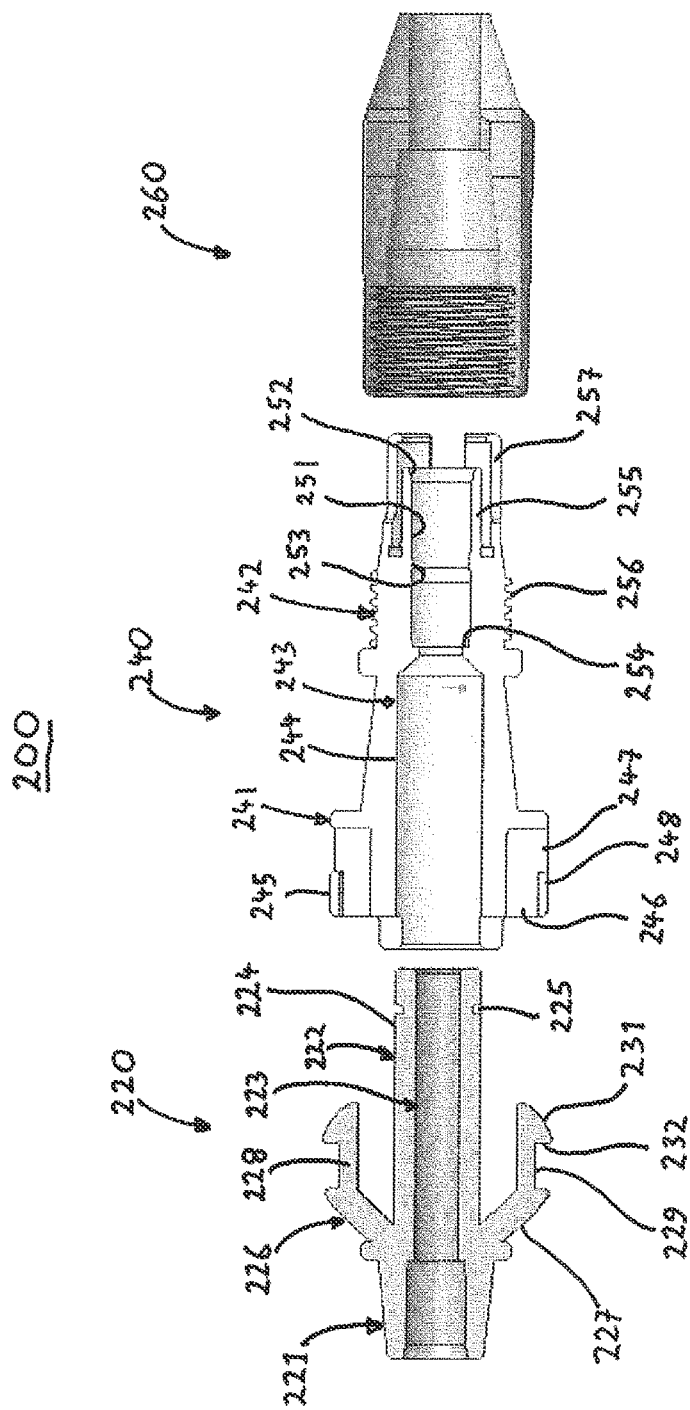
FIG. 3 shows a longitudinal cross-sectional view of a third embodiment of a connector assembly according to the invention.

Referring to FIG. 3, the connector assembly 200 according to this embodiment comprises a connector piece 220, a connector body 240, and a clamping collar 260. The connector piece 220 comprises a proximal portion 221, a distal portion 222, and a central longitudinal bore 223.

The proximal portion 221 of the connector piece 220 is configured for substantially liquid-tight connection to an inlet and/or effluent line of the peritoneal dialysis cycler such that the longitudinal bore 223 is in liquid communication with the said inlet and/or effluent line. The distal portion of the connector piece 220 comprises a substantially cylindrical nozzle 224 through which the central longitudinal bore extends. In this embodiment, the substantially cylindrical nozzle 224 is provided with a circumferential groove 225 on the radially outer surface thereof for receiving an O-ring for forming a seal with the connector body, as described further below. Alternative embodiments may have different sealing elements extending around the radially outer surface of the substantially cylindrical nozzle, for example integrally formed circumferential sealing ribs.

Two snap-fitting arms 226 extend from the proximal portion of the connector piece 220. Each arm comprises a first, outwardly projecting portion 227 and a second, longitudinally extending portion 228. A recess 229 is defined in the radially outer surface of the second, longitudinally extending portion 227 for snap-fit engagement with a corresponding retaining projection on the connector body as explained below. The distal end portions of the snap-fitting arms 226 have a ramped distal surface 231, and a retaining surface 232 oriented perpendicular to the longitudinal axis of the connector piece, for snap-fit and quick-release engagement of the connector piece on the connector body as explained further below.

The connector body 240 comprises a proximal portion 241, a distal portion 242, and a central longitudinal bore 243 extending through both. A proximal portion 244 of the central bore 243 is shaped and configured to receive the cylindrical nozzle 224 form a liquid-tight fluid coupling with the connector piece 220. An outer surface of the proximal portion 241 of the connector body 240 is provided with a plurality of radially projecting snap-fitting elements 245 for releasable snap-fitting engagement with the snap-fitting arms 226 of the connector piece. Each snap-fitting element 245 defines a longitudinally extending slot 246 for receiving the longitudinally extending portion 228 of the snap-fitting arm. An opening 247 is provided in a radially outer wall 248 of the snap-fitting element. In use, as the cylindrical nozzle 224 is inserted into the proximal portion 244 of the bore 243, the ramped distal surfaces 231 of the distal end portions of the snap-fitting arms engage the slots 246 to flex the distal end portions resiliently radially inwardly and to guide the distal end portions into the slots 246. Upon complete insertion of the cylindrical nozzle 224 into the proximal portion 244 of the bore 243, the distal end portions 230 of the snap-fitting arms snap resiliently outwardly into the openings 247. The connector piece is then retained in sealing fluid communication with the connector body by abutment between the retaining surfaces 232 of the distal portion of the snap-fitting arms and an outer wall 248 of the snap-fitting slot. To separate the connector piece from the connector body it is merely necessary for a user to press inwardly on the distal end portions of the snap-fitting arms to release the snap fitting, and pull the connector body and connector piece apart. It can thus be seen that this snap-fitting arrangement provides easy and secure releasable attachment of the connector piece to the connector body.

The distal portion 242 of the connector body 240 defines a distal portion of the central longitudinal bore extending therethrough. The distal portion of the central longitudinal bore defines a substantially cylindrical inner surface 251, a flared opening 252 at the distal end of the bore, a circumferential sealing rib 253 located on the cylindrical inner sealing surface, and a circumferential stop projection 254 located proximally of the sealing rib at the proximal end of the cylindrical inner surface 251. The diameter of the cylindrical inner surface 251 is selected to form an interference fit with a catheter transfer set tube inserted into the distal end of the longitudinal bore. The flared opening 252 facilitates insertion of the end of the tube into the bore. The circumferential sealing rib 253 presses against an outer surface of the tube to ensure a liquid-tight coupling between the connector body and the tube. Barbs (not shown) may be provided to further retain the tube in the connector body. The circumferential stop projection 254 abuts the terminal end of the tube to block further insertion of the tube beyond the desired distance. The distal-most portion of the longitudinal bore is defined by a relatively thin-walled nozzle portion 255 of the connector body.

The distal portion 242 of the connector body 240 further comprises a thread 256 on an outer surface thereof, and a distally extending split collar made up of a plurality of arcuate segments 257 circumferentially spaced around the distal nozzle, each arcuate segment having a distal, radially-inwardly projecting flange.

The structure and function of the plurality of the threads 256, the arcuate segments 257, and the clamping collar 260 to effect cut-off of liquid flow through the connector are substantially similar to those described in relation to the corresponding elements of the embodiment of FIG. 2, and therefore will not be described further. Likewise, the threads 256 may be replaced by pins in combination with helical/bayonet-type slots as described above.

In all embodiments, one or more of the connector piece, the connector body, the clamping collar (where present), and the end caps (where present) may suitably each be integrally formed in one piece by injection molding of a thermoplastic material. Any suitable rigid, chemical and creep-resistant medically acceptable plastic which is sterilizable and injection moldable is suitable. For example, the thermoplastic may comprise a polycarbonate, polyurethane, or other suitable hard plastic.

It will be appreciated that features disclosed in connection with any one of the above embodiments may be present in any other of the disclosed embodiments. Thus, for example, the screw-fitting connection between the connector piece and the connector body described in relation to the embodiments of FIGS. 1 and 2 may replace the snap-fitting connection in the embodiment of FIG. 3, and vice-versa. The skilled person will identify various other modifications falling within the scope of the accompanying claims.

The invention claimed is:

1. A connector assembly configured to connect a tube to a peritoneal dialysis cycler, the connector assembly comprising:
   a connector piece having a proximal portion and a distal portion and having a bore extending longitudinally therethrough, wherein a proximal end of the bore of the connector piece defines an opening in the proximal portion of the connector piece configured to receive and deliver fluid from and to the peritoneal dialysis cycler, and wherein a distal end of the bore defines an opening in the distal portion of the connector piece; and
   a connector body having a proximal portion and a distal portion and having a bore extending longitudinally therethrough, wherein a proximal end of the bore of the connector body defines a cavity in the proximal portion of the connector body configured to receive the distal portion of the connector piece to position the distal end of the bore of the connector piece in fluid communication with the proximal end of the bore of the connector body, the distal portion of the connector body comprising a tubular portion configured to form an interference fit with an end of the tube, and wherein the connector body further comprises a distally extending collar configured to grip an outer surface of the tube when the tube forms the interference fit with the tubular portion,
   wherein an inner surface of the distally extending collar of the connector body is free of threading,
   wherein the distal portion of the connector piece defines a distally tapered surface extending to a distal end of the connector piece,
   wherein the distal portion of the connector piece defines a cylindrical skirt portion radially outwards of the distally tapered surface and extending to the distal end of the connector piece, the cylindrical skirt portion defining a mating surface configured to releasably secure the connector piece to the connector body, and
   wherein the connector piece has an overall substantially cylindrical outer surface contiguous with and having a same diameter as the cylindrical skirt portion.

2. The connector assembly of claim 1, wherein the distally tapered surface is configured to form an interference fit with a correspondingly tapered inner surface of the proximal end of the bore of the connector body.

3. The connector assembly of claim 1, wherein the connector piece and the connector body comprise complementary releasable securing elements configured to releasably secure the connector piece to the connector body.

4. The connector assembly of claim 3, wherein the distal portion of the connector piece comprises a central nozzle, the central nozzle defining the distally tapered surface, the cylindrical skirt portion extending distally around and radially spaced from the central nozzle, the cylindrical skirt portion defining a first thread on the mating surface, wherein the mating surface is an internal surface of the cylindrical skirt portion, and wherein the proximal portion of the connector body comprises a second thread on an outer surface thereof configured to releasably secure the connector body to the connector piece by engagement of the first thread and the second thread.

5. The connector assembly of claim 3, wherein the complementary releasable securing elements comprise snap-fitting elements.

6. The connector assembly of claim 5, wherein the snap-fitting elements comprise one or more flexible arms fixed to the connector piece, and wherein the one or more flexible arms are configured to engage complementary recesses in the connector body to releasably secure the connector piece to the connector body.

7. The connector assembly of claim 1, wherein the tubular portion of the connector body comprises a tapered nozzle configured to form the interference fit with an interior surface of the end of the tube.

8. The connector assembly of claim 7, wherein the inner surface of the distally extending collar and an outer surface of the tubular portion define an annular gap therebetween configured to receive a wall of the tube, and wherein a width of the annular gap tapers proximally.

9. The connector assembly of claim 1, wherein a distal portion of the bore of the connector body is configured to receive the tube and to form the interference fit with the outer surface of the tube.

10. The connector assembly of claim 9, wherein the distal portion of the bore of the connector body comprises one or more inwardly extending annular sealing elements.

11. The connector assembly of claim 1, wherein the distally extending collar comprises one or more inwardly extending radial projections or barbs configured to grip the outer surface of the tube.

12. The connector assembly of claim 1, wherein a distal end of the distally extending collar is located distally of the distal end of the bore of the connector body.

13. The connector assembly of claim 12, wherein at least a distal portion of the distally extending collar is segmented, having a plurality of circumferentially spaced distally extending segments separated by an equal plurality of gaps, each segment of the plurality of circumferentially spaced distally extending segments having a respective distal flange extending radially inwardly, the connector assembly further comprising a clamping collar having a bore with a distally tapered internal surface, wherein proximal movement of the clamping collar onto the distal portion of the connector body causes an internal surface of the bore of the clamping collar to abut the plurality of circumferentially spaced distally extending segments to drive the plurality of circumferentially spaced distally extending segments radially inwardly to cut off a liquid path through the connector assembly.

14. The connector assembly of claim 13, wherein an outer surface of the distal portion of the connector body and an inner surface of a proximal portion of the clamping collar comprise complementary threads, whereby the connector body and the clamping collar are configured such that screwing the clamping collar onto the distal portion of the connector body drives the clamping collar proximally onto the connector body to cut off the liquid path through the connector assembly.

15. The connector assembly of claim 1, wherein the distal portion of the connector body and the distally extending collar are integrally formed in one piece.

16. The connector assembly of claim 1, wherein a distal end of the connector body is configured to be attached to a peritoneal dialysis catheter transfer set in fluid communication with the bore of the connector body.

17. The connector assembly of claim 1, wherein a proximal end of the connector piece is configured to be attached to a source of peritoneal dialysate in fluid communication with the bore of the connector piece.

* * * * *